(12) United States Patent
Rotaru

(10) Patent No.: US 9,739,995 B2
(45) Date of Patent: Aug. 22, 2017

(54) OPERATING SYSTEM AND METHOD FOR DISPLAYING AN OPERATING AREA

(75) Inventor: Calin Augustin Rotaru, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 13 days.

(21) Appl. No.: 14/350,487

(22) PCT Filed: Aug. 27, 2012

(86) PCT No.: PCT/EP2012/066565
§ 371 (c)(1),
(2), (4) Date: Aug. 4, 2014

(87) PCT Pub. No.: WO2013/053529
PCT Pub. Date: Apr. 18, 2013

(65) Prior Publication Data
US 2014/0354593 A1 Dec. 4, 2014

(30) Foreign Application Priority Data

Oct. 12, 2011 (DE) .................. 10 2011 084 345

(51) Int. Cl.
*G09G 1/00* (2006.01)
*G02B 21/36* (2006.01)
*G02B 21/00* (2006.01)
*G01N 21/64* (2006.01)
*G02B 21/16* (2006.01)
(Continued)

(52) U.S. Cl.
CPC ....... *G02B 21/367* (2013.01); *G01N 21/6458* (2013.01); *G02B 21/0076* (2013.01); *G02B 21/16* (2013.01); *G02B 21/361* (2013.01); *G02B 27/58* (2013.01); *G06F 3/044* (2013.01); *G06F 3/0412* (2013.01)

(58) Field of Classification Search
CPC .......... G06F 3/033; G06F 1/00; G06F 3/0482; G06F 3/17; G06F 3/13; H04L 1/00
See application file for complete search history.

(56) References Cited

U.S. PATENT DOCUMENTS

2011/0179387 A1 7/2011 Shaffer et al.
2011/0225524 A1 9/2011 Cifra
(Continued)

FOREIGN PATENT DOCUMENTS

CN 1166417 A 12/1997
DE 10 2006 047 653 4/2008
(Continued)

OTHER PUBLICATIONS

International Search Report for PCT/EP2012/066565, dated Oct. 26, 2012.

*Primary Examiner* — Michael Faragalla
(74) *Attorney, Agent, or Firm* — Norton Rose Fulbright US LLP; Gerard Messina

(57) ABSTRACT

An operating system for a motor vehicle includes: a display device for displaying an operating area, and an operating unit which has a sensor device for detecting the approach and the position of at least one finger of a user to the operating unit. In this case, if the sensor device detects that two or more fingers are undershooting a specifiable minimum distance from the operating unit and are carrying out a first specifiable motion, an additional operating area is displayed in addition or alternatively to the operating area.

23 Claims, 2 Drawing Sheets

(51) Int. Cl.
G02B 27/58 (2006.01)
G06F 3/041 (2006.01)
G06F 3/044 (2006.01)

(56) References Cited

U.S. PATENT DOCUMENTS

2012/0023462 A1* 1/2012 Rosing et al. ............... 715/863
2012/0113028 A1* 5/2012 Marsden et al. ............. 345/173

FOREIGN PATENT DOCUMENTS

| DE | 10 2009 032 069 | 1/2011 |
| DE | 10 2009 043 719 | 4/2011 |
| DE | 10 2010 009 622 | 9/2011 |
| WO | WO 2011/105996 | 9/2011 |

* cited by examiner

OPERATING SYSTEM AND METHOD FOR DISPLAYING AN OPERATING AREA

BACKGROUND OF THE INVENTION

1. Field of the Invention

The present invention relates to an operating system for a motor vehicle having a display device for displaying an operating area and having an operating unit which has a sensor device for detecting the approach and the position of at least one finger of a user to the operating unit.

2. Description of the Related Art

Methods and devices of the type described at the outset are known from the related art. Thus, for example, published German patent application document DE 10 2006 047 653 A1 shows an operating system for a motor vehicle having a display device on which an operating area is shown having a plurality of operating fields, as well as a sensor device which detects the approach of at least one finger of a user to the operating unit and assigns the position of the finger with respect to the sensor device to one of the operating fields shown on the display unit. In the process, the operating field thereby determined is enlarged in comparison to the remaining operating fields if the finger is located in the corresponding position longer than a predetermined time period. Because of this, it is intended that the selection of the appropriate operating field be simplified for the user.

BRIEF SUMMARY OF THE INVENTION

The operating system according to the present invention has the advantage compared to the known system that the user of the operating system is able, in a simple manner, to change from the displayed operating area to another additional operating area or additionally to fade in the additional operating area, in order then to be able to select appropriate functions on it. The operating system is distinguished by the fact that, when the sensor device detects that two or more fingers, preferably three fingers of the user undershoot a specified minimum distance from the operating unit and carry out a first specifiable motion, an additional operating area is displayed additionally or alternatively to the operating area or rather to the originally displayed operating area. That is, if the user approaches the sensor device, using two or more fingers, in such a way that the minimum distance is undershot, and if the user then, using these fingers, carries out the first specifiable motion, the original operating area is changed to the extent that, either a new additional operating area is displayed, having new operating possibilities or functions instead of the original operating area, or is faded in over the current operating area, at least in some areas.

Moreover, it is preferably provided that the additional operating area is displayed only when the minimum distance has been undershot so far in the execution of the motion that the distance of the fingers from the sensor device is equal to zero, so that the fingers are touching the sensor device. According to this specific embodiment, consequently, a touching contact is provided to let the desired operating field change take place.

The sensor device is developed particularly preferably as a capacitively working sensor field. Such sensor devices have become known, for example, by the term "touch pad" in the computer field. Consequently, known components are able to be used for the operating unit, which leads to cost savings.

In a particularly preferred manner, the sensor device is integrated into the display device, to form a screen that is sensitive to the approach and/or the touch. Thus, a so-called touch screen is provided, that is, a screen sensitive to being touched, so that the user does not have to position his finger blindly on a separate sensor device, but rather is able to position it directly over the displayed element of the operating area.

According to one advantageous refinement of the present invention, it is provided that, in response to another, second specifiable motion, the additional operating area is faded out again. The second motion is particularly a motion in the opposite direction to that of the first motion. With that, using the motions and gestures known to him, the user is able to fade in and fade out the additional operating area, preferably independently of what is displayed on the originally displayed operating area. Consequently, the user is always able to change the additional menu displayed on the additional operating area, for example. The only assumption for this is that his fingers, in the desired number, undershoot the minimum distance and carry out the respective motion.

It is provided particularly preferably that, in response to the detection of at least one other, third specifiable motion, a change be made from the additional operating area to at least one further additional operating area. It is conceivable, for example, that one might change between a plurality of submenus of the additional operating area, using the third motion or gesture. It is particularly preferred if the first motion is a vertical motion and the second motion is also a vertical one, but in the opposite direction from the first motion, while the third motion is preferably executed perpendicular to the first and/or second motion, and, using a fourth motion, which is preferably opposite to the third motion, one being able to change back to the original additional operating area, for instance. In this way, one is able to leaf through a plurality of submenus of the additional operating area in two directions.

The operating system preferably includes a time switch for monitoring an approach of the fingers to the sensor device or to the operating unit below the specifiable minimum distance. In this context, it is provided that a supplementary information is displayed on the operating area if the predefined duration in the case of the approach is exceeded. It is thereby possible, in a simple manner, for the user to have displayed to him additional data on the operating area or the additional operating area, if he only puts the two or three fingers into the vicinity of the operating unit or the sensor device, which undershoot the minimum distance and are not used during the specifiable time period.

According to one advantageous refinement of the present invention, it is provided that, if the fingers undershoot the minimum distance, particularly for a predetermined time period, without however carrying out a motion or a gesture, on the operating area, at least one additional information at least with respect to an operating element of the operating area that corresponds to the position of the fingers is displayed. It may also be provided that, if only two fingers undershoot the minimum distance without being moved, particularly after reaching the time period, additional information is only displayed with respect to the operating element corresponding to the position of the finger, and if three fingers undershoot the minimum distance, especially for the predetermined time period, additional information, such as an information text or an auxiliary text is displayed or faded into each operating element on the operating area.

It is particularly preferred if the additional operating area is only faded in if the two or more fingers of the user touch the operating unit or the sensor device. If they only approach the sensor device, then, as was described before, at least one additional information is faded in on the existing operating area.

DETAILED DESCRIPTION OF THE INVENTION

Figure 1:
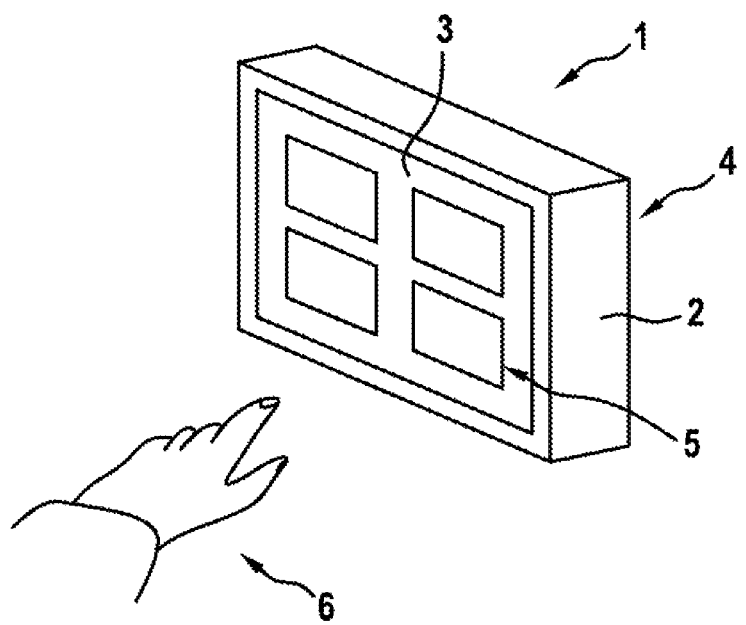
FIGS. 1 through 3 show the operation of an advantageous operating system in a plurality of steps.

FIG. 1, in a simplified illustration, shows an operating system 1 of a motor vehicle which, in particular, forms the communications interface between the driver and at least one device of the motor vehicle, especially a navigation system, an entertainment system or the like. Operating system 1 has a display device 2 which is designed as a screen or display. Integrated into display device 2 is a sensor device 3, developed as an operating unit 4, which extends at least over the display area of display device 2 as a capacitive sensor field, so that a screen is provided that is sensitive to approach and touch. Display device 2, in its initial setting, displays an operating area 5, which, in this exemplary embodiment, has a plurality of square-shaped operating elements, which are situated in a matrix-like manner. As is also true in the usual touch-sensitive screens, operating system 1 is able to be operated by touching the operating elements shown of operating area 5, so as to trigger the appropriate functions.

Thus, if hand 6 of a user approaches operating system 1 and if a finger of the user presses one of the operating fields, a navigation process is started, for example or the radio is switched on or off.

Figure 2:
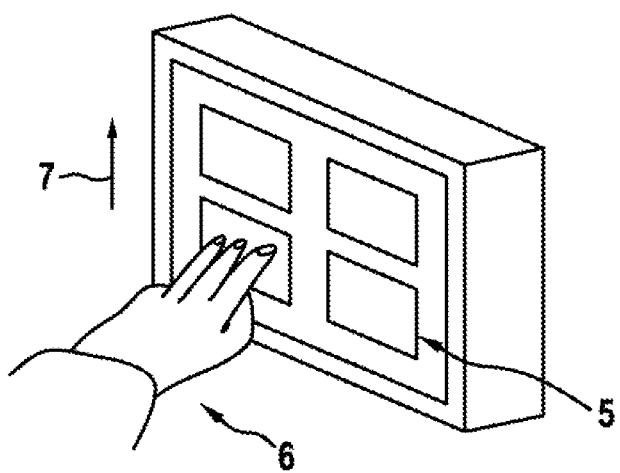
Figure 3:
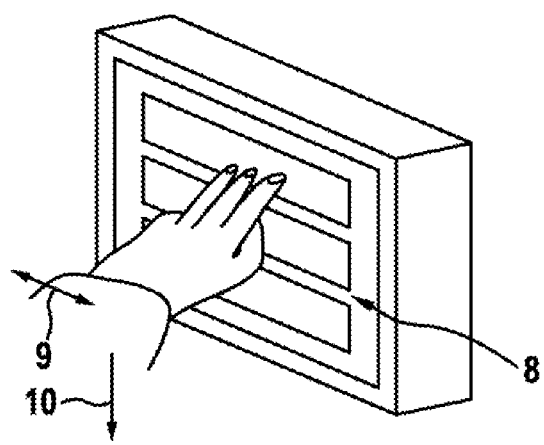

As shown in FIG. 2, a motion of hand 6 of the user is advantageously detected if the user, as in the present exemplary embodiment, approaches the sensor device or screen 5 with three fingers so closely that a specifiable minimum distance from the fingers to operating unit 4 is undershot, or the fingers touch the sensor device/operating system 1. If the user then moves his hand 6 upwards, as is indicated by an arrow 7, instead of operating area 5, an additional operating area 8 is faded in, as is shown, for example, in FIG. 3. By contrast to original operating field 5, additional operating field 8 has a plurality of rectangular operating elements situated below one another, which lead to further functions of the motor vehicle. If the user then moves his three fingers horizontally to the left or right, as is shown by a double arrow 9, further sides of the additional operating area are displayed, so that the user is able to leaf through a multitude of submenus. In order to return to original operating area 5, the user moves his three fingers 6 vertically downwards, which is indicated by an arrow 10. In this context, the motions must constantly be carried out at an undershot minimum distance.

Consequently, the present invention enables the user at any time to call up the additional operating field, by moving his three fingers vertically upwards during the undershooting of the minimum distance. By horizontal motions, the user may then change between various submenus or pages of the additional operating area, and by a vertical motion downwards, he may return again to the original operating area. Thus, the various gestures represent motions that are schematically summarized in FIG. 4.

Figure 4:
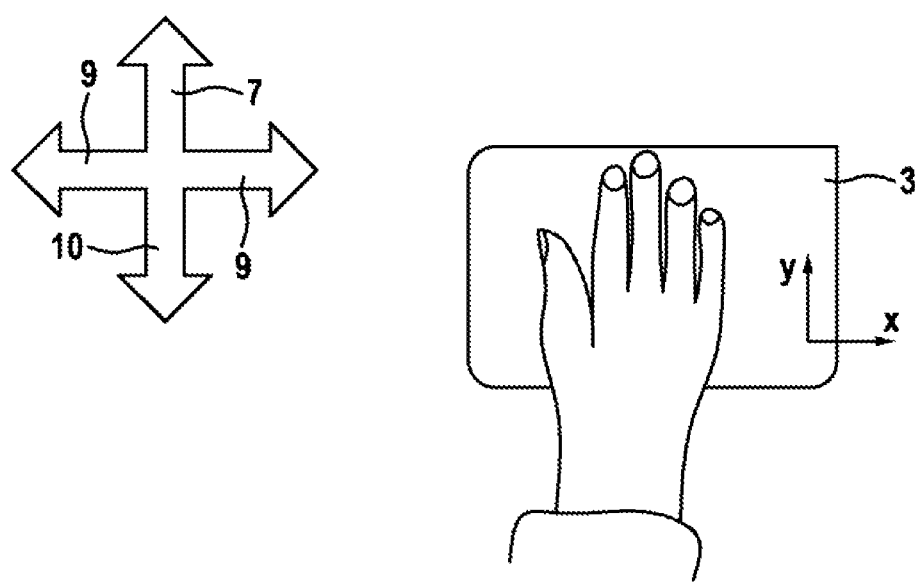
FIG. 4 shows a gesture control for the operating system in a simplified illustration.

FIG. 4 additionally shows an alternative development in which the sensor device is not developed as a component of display device 2, but is present separately as a touch pad.

According to one further exemplary embodiment of operating system 1 that is not shown here, it is provided that, if the user approaches his three fingers so closely to sensor device 3 that the minimum distance is undershot, sensor device 3 not being touched, however, and the fingers not being moved for a specifiable time period, additional data are shown on operating area 5 or 8 which, for example, relate to an operating element of operating area 5 or 8 corresponding to the position of the fingers, such as an information text, such as on the effects which the clicking or touching of the operating elements have. It is particularly advantageous if the user does not move his fingers for a second time period, beyond the first time period in order to display additional data to each operating element or an auxiliary page.

All in all, operating system 1 permits the user a rapid and effective utilization, since he is able, in a simple manner, to change between different operating areas and, if necessary, let additional data be displayed.

Preferably, for the determination of the direction of motion of the fingers, the end and start coordinates, that is, the starting position and the ending position of the fingers are used on the sensor device and the sensor field, respectively. In order to limit operating errors and measuring errors, motions that are not carried out vertically or horizontally but in a 45° angular range, are ignored. An angle deviating from the exactly horizontal or vertical motion is assigned to the horizontal or the vertical motion, corresponding to the angular segment in which it is located. A motion, for instance, at an angle of 84° with respect to an X-Y coordinate system, as is indicated in FIG. 4, will thus be detected as a vertical upward motion, corresponding to arrow 7, and a corresponding function, namely the displaying of the additional operating field, is carried out. Other specifiable motions for displaying and leafing through the additional operating field may naturally also be provided.

Thus, the motion in the direction of arrow 7 is a first motion, a motion in the direction of arrow 10 is a second motion, opposite the first motion, and a horizontal motion in respectively one direction of double arrow 9 is in each case a third motion.

What is claimed is:

1. An operating system for a motor vehicle, comprising:
a display device for displaying at least a first operating area; and
an operating unit which has a sensor device for detecting at least an approach and a position of at least one finger of a user relative to the operating unit;
wherein in the case the sensor device detects at least two fingers are (i) closer than a specified minimum distance from the operating unit and (ii) carrying out a first specified motion, a second operating area is displayed one of in addition or alternatively to the first operating area,
wherein the second operating area has second operating elements that are different than first operating elements of the first operating area, and
wherein the plurality of operating elements is situated in a matrix.

2. The operating system as recited in claim 1, wherein the sensor device is integrated into the display device to form a screen which is sensitive to at least one of a touch and an approach of at least one finger.

3. The operating system as recited in claim 2, wherein the second operating area is displayed if the at least two fingers touch the operating unit.

4. The operating system as recited in claim 2, wherein the sensor device includes a capacitive sensor field.

5. The operating system as recited in claim 3, wherein, in response to a detection of another, second specified motion, the second operating area is faded out.

6. The operating system as recited in claim 3, wherein, in response to a detection of at least one other, third specified motion, a change is made from the second operating area to at least one further additional operating area.

7. The operating system as recited in claim 2, further comprising:
a time switch for ascertaining a duration of the at least two fingers being closer than the specified minimum distance to the operating unit, wherein at least one additional information is displayed in the case the ascertained duration exceeds a specified maximum duration.

8. A method for displaying at least one operating area of an operating system for a motor vehicle by a display device, comprising:
detecting, by a sensor device, at least an approach and a position of at least one finger of a user relative to an operating unit of the operating system; and
displaying a second operating area one of in addition or alternatively to the first operating area, in the case the sensor device detects at least two fingers which are (i) closer than a specified minimum distance from the operating unit and (ii) carrying out a first specified motion,
wherein the second operating area has second operating elements that are different than first operating elements of the first operating area, and
wherein the plurality of operating elements is situated in a matrix.

9. The operating system as recited in claim 8, wherein at least one of the first operating area and the second operating area includes the at least one submenu or at least one page.

10. The operating system as recited in claim 5, wherein the second specified motion is a motion in a direction opposite to a direction of the first specified motion.

11. The operating system as recited in claim 10, wherein using the first specified motion and the second specified motion the second operating area is one of faded in and faded out independently of the displayed first operating area.

12. The operating system as recited in claim 6, wherein the first specified motion and the second specified motion are both one of a vertical motion and a horizontal motion, while the third specified motion is the other one of the vertical motion and the horizontal motion.

13. The operating system as recited in claim 6, wherein a fourth specified motion is a motion in a direction opposite to a direction of the third specified motion.

14. The operating system as recited in claim 7, wherein the at least one additional information displayed is based on a position of the detected at least two finders.

15. The operating system as recited in claim 12, wherein the vertical motion includes a 45 degree angular range around each side of a vertical axis and wherein the horizontal motion includes a 45 degree angular range around each side of a horizontal axis.

16. The operating system as recited in claim 14, wherein the at least one additional information includes an information text or an auxiliary text in each of operating elements in at least one of the first operating area and the second operating area.

17. The operating system as recited in claim 5, wherein when the second operating area is faded out due to the detection of the second specified motion, the first operating area is faded back in.

18. The operating system as recited in claim 1, wherein at least one of the first operating area and the second operating area includes a plurality of operating elements from which each element is selectable to trigger a respective function.

19. The operating system as recited in claim 1, wherein each of the first operating area and the second operating area includes a plurality of operating elements from which each element is selectable to trigger a respective function.

20. The operating system as recited in claim 1, wherein the at least one finger includes three fingers, wherein a vertical motion of the three fingers calls up the second operating area, and wherein a horizontal motion of the three fingers shows at least one submenu of the second operating area.

21. An operating system for a motor vehicle, comprising:
a display device for displaying at least a first operating area; and
an operating unit which has a sensor device for detecting at least an approach and a position of at least one finger of a user relative to the operating unit;
wherein in the case the sensor device detects at least two fingers are (i) closer than a specified minimum distance from the operating unit and (ii) carrying out a first specified motion, a second operating area is displayed one of in addition or alternatively to the first operating area,
wherein the at least one finger includes three fingers, wherein a vertical motion of the three fingers calls up the second operating area, and wherein a horizontal motion of the three fingers shows at least one submenu of the second operating area, and
wherein determination of the direction of motion of the three fingers, a starting position and an ending position of the three fingers are used on the sensor device and the sensor field, respectively, and wherein to limit at least one of an operating error and a measuring error, a motion that is not carried out vertically or horizontally, but in a 45° angular range, is ignored.

22. The method as recited in claim 8, wherein the at least one finger includes three fingers, wherein a vertical motion of the three fingers calls up the second operating area, and wherein a horizontal motion of the three fingers shows at least one submenu of the second operating area.

23. A method for displaying at least one operating area of an operating system for a motor vehicle by a display device, comprising:
detecting, by a sensor device, at least an approach and a position of at least one finger of a user relative to an operating unit of the operating system; and
displaying a second operating area one of in addition or alternatively to the first operating area, in the case the sensor device detects at least two fingers which are (i) closer than a specified minimum distance from the operating unit and (ii) carrying out a first specified motion;
wherein the at least one finger includes three fingers, wherein a vertical motion of the three fingers calls up the second operating area, and wherein a horizontal motion of the three fingers shows at least one submenu of the second operating area, and
wherein determination of the direction of motion of the three fingers, a starting position and an ending position of the three fingers are used on the sensor device and the sensor field, respectively, and wherein to limit at least one of an operating error and a measuring error, a motion that is not carried out vertically or horizontally, but in a 45° angular range, is ignored.

* * * * *